US006929799B2

(12) United States Patent
Barletta et al.

(10) Patent No.: US 6,929,799 B2
(45) Date of Patent: Aug. 16, 2005

(54) D-ALANINE RACEMASE MUTANTS OF MYCOBACTERIA AND USES THEREFORE

(75) Inventors: Raul G. Barletta, Lincoln, NE (US); Ofelia Barletta-Chacon, Lincoln, NE (US)

(73) Assignee: Board of Regents University of Nebraska-Lincoln, Lincoln, NE (US)

( * ) Notice: Subject to any disclaimer, the term of this patent is extended or adjusted under 35 U.S.C. 154(b) by 0 days.

(21) Appl. No.: 10/323,351

(22) Filed: Dec. 18, 2002

(65) Prior Publication Data

US 2003/0133952 A1 Jul. 17, 2003

Related U.S. Application Data

(60) Provisional application No. 60/341,485, filed on Dec. 18, 2001.

(51) Int. Cl.[7] .......................... A61K 39/04; A61K 39/02; C12N 1/00

(52) U.S. Cl. .................... 424/248.1; 424/9.2; 424/93.1; 424/93.2; 424/184.1; 424/200.1; 424/234.1; 424/9.1; 435/243; 435/252.1; 435/253.1

(58) Field of Search ........................ 424/9.1, 9.2, 93.1, 424/93.2, 184.1, 200.1, 234.1, 248; 435/243, 253.1, 252.1

(56) References Cited

PUBLICATIONS

Brown, Barbara A., et al., "*Mycobacterium wolinskyi* Sp. Nov. and *Mycobacterium goodii* Sp. Nov., Two New Rapidly Growing Species Related to *Mycobacterium smegmatis* and Associated with Human Would Infections: A Cooperative Study from the International Working Group on Mycobacterial Taxonomy", *International Journal of Systematic Bacteriology.* 1999, vol. 49, p. 1493–1511.
Hingley–Wilson, Suzanne M., et al., "Survival Perspectives from the World's Most Successful Pathogen, *Mycobacterium tuberculosis*", *Nature Immunology.* Oct. 2003, vol. 4, No. 10, p. 949–955.
Lagier, Beatrice, et al., "Identification of Genetic Loci Implicated in the Survival of *Mycobacterium smegmatis* in Human Mononuclear Phagocytes", *Molecular Microbiology.* 1998, vol. 29, No. 2, p. 465–475.
Piddington, Debra L., et al., "Cu,Zn Superoxide Dismutase of *Mycobacterium tuberculosis* Contributes to Survival in Activated Macrophages That Are Generating an Oxidative Burst", *Infection and Immunity.* Aug. 2001, vol. 69, No. 8, p. 4980–4987.
Harth Gunter, et al., "High–Level Heterologous Expression and Secretion in Rapidly Growing Nonpathogenic Mycobacteria of Four Major Mycobacterium tuberculosis Extracellular Proteins Considered To Be Leading Vaccine Candidates and Drug Targets", *Infection and Immunity,*. Jun. 1997, vol. 65, No. 6, p. 2321–2328.

MacGowan, Alasdair, et al., "In Vitro Models, In Vivo Models, and Pharmacokinetics: What Can We Learn from In Vitro Models?", *CID.* 2001 vol. 33 (Suppl 3), p. S214–S220.
Orme, Ian M. and Collins, Frank M., "Mouse Model of Tuberculosis". Chapter 8, p. 113–134. *Tuberculosis: Pathogenesis, Protection and Control,* Barry R. Bloom (ed.), 1994, American Society for Microbiology, Washington, DC 20005.
McMurray, David N., "Guinea Pig Model of Tuberculosis". Chapter 9, p. 135–147. *Tuberculosis: Pathogenesis, Protection and Control,* Barry R. Bloom (ed.), 1994, American Society for Microbiology, Washington, DC 20005.
Dannenberg, Jr., Arthur M., "Rabbit Model of Tuberculosis". Chapter 10, p. 149–156. *Tuberculosis: Pathogenesis, Protection and Control,* Barry R. Bloom (ed.), 1994, American Society for Microbiology, Washington, DC 20005.
Thoen, Charles O., "Tuberculosis in Wild and Domestic Mammals". Chapter 11, p. 157–162. *Tuberculosis: Pathogenesis, Protection and Control,* Barry R. Bloom (ed.), 1994, American Society for Microbiology, Washington, DC 20005.
Jacobs, Jr., William R. "*Mycobacterium tuberculosis:* A Once Genetically Intractable Organism", p. 1–16, *Molecular Genetics of Mycobacteria,* G.F. Halful and W.R. Jacobs, Jr., (eds.)., 2000, ASM Press, Washington, D.C.
Tyagi, Jaya Sivaswami and Sharma, Deepak "*Mycobacterium smegmatis* and Tuberculosis", *Trends in Microbiology.* Feb. 2002, vol. 10, No. 2, p. 68–69.
David Hugo L., et al., "Susceptibility of Mycobacterial D–Alanyl–D–Alanine Synthetase to D–Cycloserine", *American Review of Respiratory Disease.* 1969, vol. 100, p. 579–581.
Neuhaus, Francis C., "The Enzymatic Synthesis of D–Alanyl–D–Alanine. I. Purification and Properties of D–Alanyl–D–Alanine .Synthetase", *Journal of Biological Chemistry.* 1962, vol. 237, No. 3, p. 778–786.

(Continued)

Primary Examiner—Rodney P Swartz
(74) Attorney, Agent, or Firm—Stinson Morrison Hecker LLP; Nancy T. Morris

(57) ABSTRACT

The present invention is directed to D-alanine racemase mutants of mycobacterial species. The D-alanine racemase gene (alrA) is involved in the systhesis of D-alanine, a basic component of peptidoglycan that forms the backbone of the bacterial cell wall. The present invention is also directed to methods of making live-attenuated vaccines against pathogenic mycobacteria using such alrA mutants and to the vaccines made according to such methods. The present invention is further directed to use of alrA mutants in methods for screening antimycobacterial agents that are synergistic with peptidoglycan inhibitors. Finally, the present invention is directed to methods to identify new pathways of D-alanine biosynthesis for use in developing new drugs targeting peptidoglycan biosynthesis in mycobacteria and to identify vaccines useful against pathogenic mycobacteria.

10 Claims, No Drawings

PUBLICATIONS

Peteroy, Marcy, et al., "Characterization of a *Mycobacterium smegmatis* Mutant That is Simultaneously Resistant to D–Cycloserine and Vancomycin", *Antimicrobial Agents and Chemotherapy.* Jun. 2000, vol. 44, No. 6, p. 1701–1704.

Manning, James M., et al., "Inhibition of Bacterial Growth by β–Chloro–D–Alanine", *Proceedings of the National Academy of Science.* Feb. 1974, vol. 71, No. 2, p. 417–421.

David Suzana, "Synergic Activity of D–Cycloserine and β–Chloro–D–Alanine Against *Mycobacterium tuberculosis*", *Journal of Antimicrobial Chemotherapy.* 2001. vol. 47, p. 203–206.

Marshall, C. Gary and Wright, Gerard D., "Dd1N from Vancomycin–Producing *Amycolatopsis Orientalis* C329.2 Is a VanA Homologue with D–Alanyl–D–Lactate Ligase Activity", *Journal of Bacteriology.* Nov. 1998, vol. 180, No. 21, p. 5792–5795.

Rastogi, Nalin, et al., "Enhancement of Drug Susceptibility of *Mycobacterium avium* by Inhibitors of Cell Envelope Synthesis", *Antimicrobial Agents and Chemotherapy.* May 1990, vol. 34, No. 5, p. 759–764.

Dutka–Malen, Slyvie, et al., "Sequence of the vanC gene of *Enterococcus gallinarum* BM4174 Encoding a D–Alanine:D–Alanine Ligase–Related Protein Necessary for Vancomycin Resistance", *Gene.* 1992, vol. 112, p. 53–58.

Belager, Aimee E. and Inamine, Julia M. "Genetics of Cell Wall Biosynthesis". Chapter 12, p. 191–202. *Molecular Genetics of Mycobacteria,* G.F. Hatful and W.R. Jacobs, Jr., (eds.)., 2000, ASM Press, Washington, D.C.

Reitz, Richard H., et al., "The Biochemical Mechanisms of Resistance by Streptococci to the Antibiotics D–Cycloserine and 0–Carbamyl–D–serine", *Biochemistry.* Aug. 1967, vol. 6, No. 8, p. 2561–2570.

Walsh, Christopher T., "Enzymes in the D–Alanine Branch of Bacterial Cell Wall Peptidoglycan Asasembly", *Journal of Biological Chemistry.* Feb. 1989, vol. 264, No. 5, p. 2393–2396.

David, Hugo L., "Resistance to D–Cycloserine in the Tubercle Bacilli: Mutation Rate and Transport of Alanine in Parental Cells and Drug–Resistant Mutants", *Applied Microbiology.* May 1971, vol. 21, No. 3, p. 888–892.

Zygmunt, Walter A., "Antagonism of D–Cycloserine Inhibition of Mycobacterial Growth by D–Alanine", *Journal of Bacteriology.* 1963, vol. 85, p. 1217–1220.

Yew, W.W., et al., "AdverseNeurological Reactions in Patients with Multidrug–Resistant Pulmonary Tuberculosis After Coadministration of Cycloserine and Ofloxacin", *CID.* Aug. 1993, vol. 17, p. 288–289.

Kaufman, Darrell S. Manley, William F., "A New Procedure for Determining DL Amino Acid Ratios In Fossils Using Reverse Phase Liquid Chromatography", *Quaternary Geochronology.* 1998, vol. 17, p. 987–1000.

Neuhaus, Francis C., "D–Cycloserine and O–Carbamyl–D–Serine", p. 40–83, *Antibiotics. vol. 1 Mechanism of Action,* David Gottlieb and Paul D. Shaw (eds.), 1967, Springer–Verlag, New York, Inc.

Barletta, Raul G., et al., "Vaccines Against Intracellular Pathogens", *Subcellular Biochemistry.* 2000, vol. 33, p. 559–599.

Barletta, Raul G., "Targeting M. Tuberculosis Alanine Ligase for Drug Design" (abstract), NIH Grant No. 1R03AI051176–01, 2002.

Feng, Zhengyu, and Barletta, Raül, "Roles of *Mycobacterium smegmatis* D–Alanine:D–Alanine Ligase and D–Alanine Racemase in the Mechanisms of Action of and Resistance to the Peptiodoglycan Inhibitor D–Cycloserine", *Antimicrobial Agents and Chemotherapy.* 2003, vol. 47, No. 1, p. 283–291.

Chacon, Ofelia, et al., "*Mycobacterium smegmatis* D–Alanine Racemase Mutants Are Not Dependent on D–Alanine for Growth", *Antimicrobial Agents and Chemotherapy.* 2002, vol. 46, No. 1, p. 47–54.

Cáceres, Nancy E., et al., "Overexpression of the D–Alanine Racemase Gene Confers Resistance to D–Cycloserine in *Mycobacterium smegmatis*", *Journal of Bacteriology.* Aug. 1997, vol. 179, No. 16, p. 5046–5055.

Zhengyu, Feng, et al., "*Mycobacterium smegmatis* L–Alanine Dehydrogenase (Ald) Is Required for Proficient Utilization of Alanine as a Sole Nitrogen Source and Sustained Anaerobic Growth", Journal of Bacteriology. Sep. 2002, vol. 184, No. 18, p. 5001–5010.

Kamogashira, Takashi and Takegata, Setsuko, "A Screening Method for Cell Wall Inhibitors Using a D–Cycloserine Hypersensitive Mutant", *The Journal of Antibiotics.* Jun. 1988, vol. XLI, No. 6, p. 803–806.

Strych, Ulrich, et al., "Characterization of the Alanine Racemases from Two Mycobacteria", *FEMS Microbiology Letters.* 2001, vol. 196, p. 93–98.

Copié, Valérie, et al., "Inhibition of Alanine Racemase by Alanine Phosphonate: Detection of an Imine Linkage to Pyridoxal 5'–Phosphate in the Enzyme–Inhibitor Complex by Solid–State $^{15}N$ Nuclear Magnetic Resonance". *Biochemistry,* 1988, vol. 27, p. 4966–4970.

Heaton, Michael P., et al, "Controlled Lysis of Bacterial Cells Utilizing Mutants with Defective Synthesis of D–Alanine", *Can. J. Microbiol.,* 1988, vol. 34, p. 256–261.

Patchett, Arthur A., et al., "Antibacterial Activities of Fluorovinyl– and Chlorovinylglycine and Several Derived Dipeptides", *Antimicrobial Agents and Chemotherapy.* Mar. 1988, vol. 32, No. 3, p. 319–323.

Lambert, Mary P., and Neuhaus, Francis C., "Mechanism of D–Cycloserine Action: Alanine Racemase from Escherichia coli W", *Journal of Bacteriology.* 1972, vol. 110, No. 3, p. 978–987.

Hols, Paxcal, et al, "Conversion of *Lactococcus Lactis* from Homolactic to Homoalanine Fermentation through Metabolic Engineering", *Nature Biotechnology.* Jun. 1999, vol. 17, p. 588–592.

Tauch, Andreas, et al., "The Alanine Racemase Gene alr is an Alternative to Antibiotic Resistance Genes in Cloning Systems for Industrial *Corynebacterium Glutamicum* Strains", *Journal of Biotechnology.* 2002, vol. 99, p. 79–91.

Arias, Cesar A., et al, "Serine and Alanine Racemase Acivities of VanT: a Protein Necessary for Vancomycin Resistance in *Enterococcus Gallinarum* BM4174", *Microbiology.* 2000, vol. 146, p. 1727–1734.

Thompson, Robert J., et al, "Pathogenicity and Immunogenicity of a *Listeria monocytogenes* Strain That Requires D–Alanine for Growth", *Infection and Immunity.* Aug. 1998, vol. 66, No. 8, p. 3552–3561.

Hols, P., et al., "The Alanine Racemase Gene is Essential for Growth of *Lactobacillus plantarum*", *Journal of Bacteriology.* Jun. 1997, vol. 179, No. 11, p. 3804–3807.

Neidhart, David J., et al., "X-ray Crystallographic Studies of the Alanine-specific Racemase from *Bacillus stearothermophilus*", *The Journal of Biological Chemistry*. 1987, vol. 262, No. 32, p. 15323–15326.

Braunstein, Miriam, et al., "Genetic Methods for Deciphering Virulence Determinants of *Mycobacterium tuberculosis*", *Virulence and Essential Gene Identification*. 2002 p. 67–99.

D-ALANINE RACEMASE MUTANTS OF MYCOBACTERIA AND USES THEREFORE

CROSS-REFERENCE TO RELATED APPLICATIONS

The present application claims priority from provisional patent application Ser. No. 60/341,485, filed Dec. 18, 2001, which is incorporated herein by reference.

STATEMENT REGARDING GOVERNMENT RIGHTS

This invention was made with government support from United States Department of Agriculture, USDA Cooperative State Research Service Project Grant No. NEB. 14-108. The Government may have certain rights in this invention.

BACKGROUND OF THE INVENTION

The present invention is directed to D-alanine racemase mutants of mycobacterial species. The D-alanine racemase gene (alrA) is involved in the synthesis of D-alanine, a basic component of peptidoglycan that forms the backbone of the bacterial cell wall. The present invention is also directed to methods of making live-attenuated vaccines against pathogenic mycobacteria using such alrA mutants and to the vaccines made according to such methods. The present invention is further directed to use of alrA mutants in methods for screening antimycobacterial agents that are synergistic with peptidoglycan inhibitors. Finally, the present invention is directed to methods to identify new pathways of D-alanine biosynthesis for use in developing new drugs targeting peptidoglycan biosynthesis in mycobacteria and to identify vaccines useful against pathogenic mycobacteria.

The publications and other materials used herein to illuminate the background of the invention or provide additional details respecting the practice, are incorporated by reference, and for convenience are referenced in the following text by author and date and are listed alphabetically by author in the appended bibliography.

Mycobacteria cause a number of diseases in humans and animals including *tuberculosis*, which is the leading cause of human death from an infectious disease in the world (Bloom & Murray, 1992). *M. tuberculosis* is the principal cause of *tuberculosis* in humans and other primates and is occasionally seen in dogs, pigs and cattle (O'Reilly & Daborn, 1995). In contrast, *M. bovis*, the etiologic agent of bovine *tuberculosis*, has a wide host range and infects ruminants, carnivores, and primates, including humans (Pritchard, 1988). For *M. bovis* and *M. tuberculosis* in both humans and animals, contaminated aerosols are the most common routes of transmission (Carleton, 1993). Other mycobacterial pathogens of importance are *M. avium, M. paratuberculosis*, and *M. leprae. M. avium* is the agent of *tuberculosis* in birds but its major significance is as an opportunistic pathogen of AIDS patients (Inderlied et al., 1993). *M. paratuberculosis* is the etiologic agent of Johne's disease, a granulomatous enteritis in ruminants and it has also been linked to a potential etiology of a type of inflammatory bowel disease (Crohn's disease) in humans (Cocito et al., 1994; Harris and Barletta, 2001). Finally, *M. leprae* infects humans and armadillos. Though leprosy in humans has low mortality, its morbidity is quite high in affected areas, estimated to have been 10–12 million in the 1980s (Noordeen, 1991). All these diseases caused by mycobacteria are characterized pathologically by the formation of granulomatous nodules (tumor-like masses caused by chronic inflammatory processes) or "tubercules" that are seen in advanced cases. Due to the significance of mycobacterial diseases, prevention and control measures, including vaccines, diagnostics and therapies are of major importance.

Microorganisms of the *M. avium* complex have achieved prominence as major opportunistic pathogens of AIDS patients. *M. avium* is naturally resistant to most firstline antituberculosis drugs (Inderlied et al., 1993). This threat to public health has been partially met by therapy with appropriate antimicrobial agents, but unfortunately drug-resistant *M. avium* and *M. tuberculosis* strains readily appear (Chaisson et al., 1994; Espinal et al., 2000), underscoring the need to develop new and more effective anti-mycobacterial agents.

*Mycobacterium smegmatis* is a fast-growing nonpathogenic mycobacterial species particularly useful in studying basic cellular processes of relevance to pathogenic mycobacteria. The D-alanine racemase gene (alrA) is involved in the synthesis of D-alanine, a basic component of peptidoglycan that forms the backbone of the cell wall. Biosynthesis of the mycobacterial cell wall has received considerable attention in the search for inhibitors useful for drug therapy (Chatterjee, 1997). These cell walls display a complex architecture of glycolipids and proteins linked to the mycolyl-arabinogalactan-peptidoglycan backbone (McNeil and Brennan, 1991). This structure is a barrier that contributes to drug resistance (Trias and Benz, 1994), and many of its components have been found to play a major role in pathogenesis (Daffe and Draper, 1998). The analysis of the *M. tuberculosis* genome sequence suggests that peptidoglycan biosynthesis in mycobacteria follows the general pathway of other bacteria, including the formation of the basic building block D-alanyl-D-alanine (Belanger and Inamine, 2000; Cole et al., 1998). D-alanine racemase (Alr) catalyzes the conversion of L-alanine into D-alanine (Julius et al., 1970), and D-alanine-D-alanine ligase catalyzes the subsequent dimerization of D-alanine into the key dipeptide D-alanyl-D-alanine (Neuhaus, 1962). The corresponding enzymes from both *Escherichia coli* (Lambert and Neuhaus, 1972; Neuhaus and Lynch, 1964) and mycobacteria (Cáceres, 1999; David et al., 1969) are inhibited by D-cycloserine (DCS), a D-alanine analog (Neuhaus, 1967). The dipeptide is then added to the UDP-tripeptide precursor by the action of the D-alanine-D-alanine adding enzyme that completes the reactions of the D-alanine branch of peptidoglycan assembly (Walsh, 1989).

DCS is particularly effective against mycobacteria albeit with marked side effects (Cummings et al., 1955; Yew et al., 1993). Moreover, overproduction of Alr in *Mycobacterium smegmatis, Mycobacterium intracellulare*, and *Mycobacterium bovis* BCG leads to a DCS-resistant phenotype. The *M. smegmatis* enzyme is inhibited by DCS in a concentration-dependent manner (Cáceres et al., 1997). Likewise, the *M. avium* and *M. tuberculosis* enzymes produced from *E. coli* recombinant clones are also inhibited by DOS (Strych et al., 2001). Nonetheless, the specific characteristics of the mycobacterial enzymes involved in peptidoglycan biosynthesis, including the essentiality of each of their functions, remain unknown. Such knowledge would be important to the design of specific inhibitors that would serve as novel bactericidal agents to treat *M. tuberculosis* and *M. avium* infections. Furthermore, the inactivation of the genes encoding for these enzymes may lead to the generation of attenuated strains of pathogenic mycobacteria that could serve as candidate vaccines against *tuberculosis*.

*M. smegmatis* has been extensively used as a model system for *M. tuberculosis* and other mycobacteria. *M.*

*smegmatis* is nonpathogenic, requiring less stringent containment facilities, and it grows at a relatively high rate in a variety of defined and nutrient-restricted media (Jacobs, 2000). *M. smegmatis* has been used to study drug resistance mechanisms (Cáceres et al., 1997; Peteroy et al., 2000; Telenti et al., 1997) and basic physiological processes including the synthesis of peptidoglycan precursors (Cirillo et al., 1998; Pavelka and Jacobs, 1996). Insights gained from these studies can then be applied to the pathogenic mycobacteria.

SUMMARY OF THE INVENTION

It is an object of the present invention to provide a D-alanine racemase mutant mycobacteria which can be used in development of treatments for diseases caused by pathogenic mycobacteria.

Accordingly, in one aspect of the present invention, a novel mycobacterial strain, comprising a D-alanine racemase mutant which is not dependent on D-alanine for growth, designated alrA mutant, is provided. The mycobacterial strain is generated from a pathogenic *mycobacterium*. Any pathogenic mycobacteria may be used in accordance with the present invention. Preferred pathogenic mycobacteria are *M. tuberculosis, M. bovis*, and all subspecies of *M. avium*.

In another aspect of the invention, a live-attenuated vaccine against pathogenic mycobacteria is provided which includes the alrA mutant, with or without additional mutations. In one embodiment of this aspect, the alrA mutant displays increased susceptibility to an antimycobacterial agent. In a second embodiment, the alrA mutant displays increased susceptibility to bacterial action of phagocytic cells. In a third embodiment, the mutant is a D-alanine dependent pathogenic *mycobacterium*.

In a further aspect of the present invention, methods for producing live-attenuated vaccines including the alrA mutant are provided.

In another aspect of the invention, a method for screening antimycobacterial agents that are synergistic with peptidoglycan inhibitors is provided.

In yet a further aspect of the invention, a method to identify new pathways of D-alanine biosynthesis is provided. The pathways so identified may be used to develop new drugs that target peptidoglycan biosynthesis in mycobacteria and to identify new vaccines useful against pathogenic mycobacteria.

DETAILED DESCRIPTION OF THE INVENTION

The present invention is directed to D-alanine racemase mutants of mycobacterial species. The D-alanine racemase gene (alrA) is involved in the synthesis of D-alanine, a basic component of peptidoglycan that forms the backbone of the bacterial cell wall. The present invention is also directed to methods of making live-attenuated vaccines against pathogenic mycobacteria using such alrA mutants and to the vaccines made according to such methods. The present invention is further directed to use of alrA mutants in methods for screening antimycobacterial agents that are synergistic with peptidoglycan inhibitors. Finally, the present invention is directed to methods to identify new pathways of D-alanine biosynthesis for use in developing new drugs targeting peptidoglycan biosynthesis in mycobacteria and to identify vaccines useful against pathogenic mycobacteria.

The present invention employs the following definitions.

"alrA" and "alr" refer to the D-alanine racemase gene, including normal alleles of the alrA gene.

"AlrA" and "Alr" refer to D-alanine racemase enzyme.

"Displays increased susceptibility to antimycobacterial agent" refers to a reduction in the minimal inhibitory concentration of the mutant strain when compared with the wild type strain.

"Displays increased susceptibility to bactericidal action of phagocytic cells" refers to a reduction in the ability of the mutant strain to survive and/or replicate in phagocytic cells when compared to the wild type strain.

A "promoter" is a DNA sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. For example, a promoter may be regulated in a tissue-specific manner such that it is only active in transcribing the associated coding region in a specific tissue type(s).

In contrast, the rate of transcription is not generally regulated by an inducing agent if the promoter is a constitutive promoter. The promoter may be tissue-geneal, also known as non-tissue-preferred, such that it is active in transcribing the associated coding region in a variety of different tissue types.

It has been discovered that the *M. smegmatis* alrA gene can be insertionally inactivated to generate AlrA null mutants. Unexpectedly, the inactivation of the alrA gene in *M. smegmatis* mutant did not result in a growth requirement for D-alanine. Given the conservation of basic processes within the genus *Mycobacterium*, a similar outcome cane be expected in all mycobacterial species. PCR and Southern blotting analyses of wild-type and mutant strains confirmed the inactivation of the alrA gene in TAM20 and TAM23 by gene replacement via a double-crossover event between the *M. smegmatis* chromosome and the linear fragment carrying the inactivated gene. Thus, alrA mutants are viable and can grow in medium without D-alanine. Complementation of the alrA mutant strain with a wild-type alrA copy restores the wild-type phenotype, indicating that properties of the mutant strain are due to the inactivation of the alrA gene rather than a polar effect on the expression of a downstream gene. The independence of *M. smegmatis* alrA mutants of D-alanine for growth indicates that this mutation does not impose an auxotrophic requirement for D-alanine. This phenotype has significant implications for the synthesis of D-alanine and peptidoglycan in *M. smegmatis* and for other mycobacterial species.

D-Alanine is an essential component for bacteria with a peptidoglycan layer structure. The essentiality of D-alanine stems from the key role of the dipeptide D-alanyl-D-alanine in the cross-linking of peptidoglycan strands (Strominger, 1962). The repeating unit of the peptidoglycan from *M. smegmatis* has a D-alanine moiety (Petit et al., 1969), and D-alanyl-D-alanine is the only product detected in a biochemical assay using partially purified extracts of *M. smegmatis* D-alanine ligase (Peteroy et al., 2000). These properties support the hypothesis that D-alanine is also an essential component for *M. smegmatis*. In the context of this hypothesis, the independence of alrA mutants of D-alanine for growth suggests that *M. smegmatis* may have alternative pathways for the biosynthesis of D-alanine. Listeria monocytogenes, for example, has been shown to possess such metabolic routes (Thompson et al., 1998).

As described in further detail herein, alrA mutant mycobacteria can be used to develop safe live-attenuated vaccines of pathogenic mycobacteria, screen for drugs that act synergistically with peptidoglycan inhibitors, and identify new pathways of D-alanine biosynthesis. In summary, the D-alanine independent phenotype of *M. smegmatis* alrA mutants suggests that *M. smegmatis* has another pathway of D-alanine biosynthesis. Given the conservation of basic physiological processes, this finding is of significance for pathogenic mycobacteria and the design of novel attenuated strains and antimycobacterial agents.

Method of Use: Development of Novel alrA Mutant Mycobacterial Strains

Novel alrA mutant pathogenic mycobacterial strains can be generated in accordance with the present invention. The generation of alrA mutants has been illustrated by preparation of *M. smegmatis* alrA mutants. However, other methods known in the art may be used to generate stable alrA mutants such as chemical mutagenesis followed by mutant enrichment, transposon mutagenesis, plasmid or phage vectors, and methods to produce unmarked in-frame deletions. The same procedures described herein may be used to inactivate the alrA gene of other pathogenic mycobacterial species in order to generate alrA mutants of such species. Such species of mycobacteria include *Mycobacterium tuberculosis*, *Mycobacterium avium*, *Mycobacterium bovis*, *Mycobacterium africanum*, and *Mycobacterium paratuberculosis* To inactivate the alrA gene in *M. smegmatis*, a DNA fragment carrying the wild-type gene was subcloned into the *E. coli* cloning vector pBlue-script II KS(+) to yield the recombinant plasmid pTAMU1 (Table 1). Then, the 1.2-kb kanamycin resistance determinant from plasmid pUC4K containing the aminoglycoside 3'-phos-photransferase type I-coding gene from transposon Tn903 (30) was inserted at the unique PstI site internal to the alrA gene. The resulting construct, pTAMU2, carries an insertionally inactivated alrA gene, which can be excised as a linear 3.2-kb BamHI-kvnI fragment (Table 1). Based on the hypotheses that D-alanine is an essential component and that AlrA is the only enzyme responsible for D-alanine biosynthesis in *M. smegmatis*, it was predicted that an alrA mutant would be dependent on D-alanine for growth. Unexpectedly, the inactivation of the alrA gene in *M. smegmatis* mutant did not result in a growth requirement for D-alanine. The step to select for this mutant was carried out in MADC agar supplemented with 50 mM D-alanine in addition to 20 ug of kanamycin per ml. Transformation of *M. smegmatis* mc$^2$155 with the 3.2-kb linear fragment carrying the inactivated alrA gene yielded 25 kanamycin-resistant transformants, and 2 of these, designated TAM20 and TAM23, were further analyzed.

TABLE 1

Strains and plasmids

| Strain or plasmid | Relevant characteristics | Source or reference |
|---|---|---|
| *E. coli* DH5a | F⁻lacZDM15 endA1 hsdR17 supE44 gyrA96 relA1 | Invitrogen Life Technologies |
| *E. coli* XL2-Blue MRF' | D(mcrA)183 D(mcrCB-hsdSMR-mrr)173 endA1 supE44 thi-1 recA1 gyrA96 relA1 lac [F' proAB lacI$^q$ZDM15 Tn10 Tet$^R$ Cam$^R$] | Stratagene |
| *M. smegmatis* mc$^2$155 | Alr$^+$, high efficiency plasmid transformation mutant of *M. smegmatis* mc$^2$6 | (37) |

TABLE 1-continued

Strains and plasmids

| Strain or plasmid | Relevant characteristics | Source or reference |
|---|---|---|
| *M. smegmatis* TAM20 | Alr⁻Kan$^R$, *M. smegmatis* alr mutant derived from mc$^2$155 | This study |
| *M. smegmatis* TAM23 | Alr⁻Kan$^R$, *M. smegmatis* alr mutant derived from mc$^2$155 | This study |
| *M. smegmatis* TAM23 (pTAMU3) | Alr⁺Hyg$^R$Kan$^R$, *M. smegmatis* alr mutant complemented with wild type gene integrated at the mycobacteriophage L5 attB site | This study |
| pBUN82 | Kan$^R$, recombinant plasmid carrying the alr gene from *M. smegmatis* mc$^2$155 in a 1.9 kb BamHI/PvuII fragment | (5) |
| pBluescript II KS + | Amp$^R$, standard *E. coli* cloning vector | Stratagene |
| pTAMU1 | Amp$^R$, pBluescript II KS + with the 1.9 kb BamHI/PvuII fragment of pBUN82 in the BamHI/EcoRV site | This study |
| pTAMU2 | Amp$^R$ Kan$^R$, pTAMU1 with the 1.24 kb PstI aph fragment of pUC4K (Pharmacia, Inc. Piscataway, N.J.) in the PstI site | This study |
| pTAMU3 | Amp$^R$Hyg$^R$, pYUB412 with the 1.9 kb BamHI/PvuII fragment of pBUN82 in the BclI/EcoRV site | This study |
| pYUB412 | Amp$^R$Hyg$^R$, *E. coli*-Mycobacterium integration-proficient vector. Integrates at the mycobacteriophage L5 attB site | (33) |

To determine whether these transformants carry an inactivated alrA gene, genomic DNA was isolated and amplified by PCR. As expected for the inactivation of the alrA gene, genomic DNA from both TAM20 and TAM23 yielded the 2.4-kb product. Southern blotting analysis was used to verify the occurrence of these recombinational events in the appropriate *M. smegmatis* strains. Genomic DNA was isolated; digested with SmaI, which cuts once within the alrA gene; transferred to a membrane; and hybridized with the wild-type alrA gene fragment as a probe. The wild-type strain mc$^2$155 gave two homologous bands of approximately 15.0 and 1.8 kb, whereas TAM20 and TAM23 yielded a mutant-type pattern with three bands of approximately 15.0, 2.2, and 1.2 kb. These patterns were as expected for the predicted recombinational events, validating the construction of the strains described herein.

The identification of only one D-alanine racemase gene in the mycobacterial genome sequencing projects suggests that *M. smegmatis* alrA mutants may be dependent on exogenous D-alanine for growth. Both mutant strains, TAM20 and TAM23, exhibited wild-type growth in MADC agar supplemented with D-alanine, giving rise to typical flat-border colonies after 3 days of incubation at 37C. In the absence of D-alanine, TAM20 and TAM23 cells were also able to grow, but colonies displayed a drier appearance with more raised borders. Complementation of TAM23 with the integrating construct pTAMU3 introduces a wild-type alrA gene at the mycobacteriophage L5 attachment site (Lee and Hatfull, 1993; Pascopella, 1994) and fully restores wild-type colony morphology. Except for these differences in colony morphology, no other observable differences were detected by light or electron microscopy when cells were grown in the presence or absence of D-alanine. Bacilli from both wild-type and mutant strains were weakly gram positive, acid fast, and displayed the same aspect of elongated rods. Likewise, at the ultrastructural level, cells did not differ in either shape, size, or thickness of the cell walls. In summary, *M. smegmatis* alrA mutants are independent of exogenous D-alanine, a property that was further confirmed by their ability to grow in MADC, as described more frilly herein, and minimal broth containing mineral salts, glycerol, pyridoxal phosphate, and Tween 80.

To determine whether M. smegmatis alrA mutants are or are not devoid of Alr activity, crude cell extracts from wild-type and mutant strains were prepared and assayed for enzyme activity. Protein extracts prepared from wild type mc$^2$155 cells grown in the presence or absence of D-alanine displayed approximately equal levels of Air activity that matched the specific activities previously reported (Cáceres et al., 1997). In contrast, extracts from TAM23 prepared from cells grown in the presence or absence of D-alanine lacked any detectable Alr activity. These extracts yielded background levels of Alr activity not significantly different from the levels obtained by replacing bovine serum albumin for TAM23 extracts in the reaction mixture. This absence of Alr activity in TAM23 extracts was not clue to the presence of an inhibitor since mixtures of TAM23 and mc$^2$155 extracts gave the Air activity proportional to the amount of enzyme present in the active extract from the wild-type strain. Furthermore, to rule out the possibility that sonic disruption may have damaged more readily protein extracts of potentially fragile TAM23 cells, LDH activity was also measured. The M. smegmatis LDH activity was found to be more sensitive to prolonged sonic disruption and provides a useful control to determine whether TAM23 extracts are enzymatically active. In contrast to the results obtained in the Alr assay, extracts from both mc$^2$155 and TAM23 displayed similar levels of LDH activity above background levels. Furthermore, complementation of TAM23 with a wild-type air gene restored Alr activity. Thus, it was concluded that inactivation of the alrA gene results in no detectable Alr activity in the M. smegmatis alrA mutant strain.

Method of Use: Generation of Live-Attenuated Vaccines

An ideal vaccine against diseases caused by mycobacteria such as tuberculosis, leprosy, and Crohn's disease in humans and Johne's disease in dairy cattle should be able to protect against the widest possible range of pathogenic bacterial isolates eliciting a strong CMI requiring presentation of both peptide and non-peptide antigens, long-lasting immunological memory, and possibly humoral immunity. Given this complexity, live attenuated vaccines may offer the best possibilities for an ideal antimycobacterial vaccine. Furthermore, this type of vaccine could potentially be administered orally as enteric-coated lyophilized tablets, thus avoiding the use of needles (Barletta et al., 1990). Additionally, a live attenuated vaccine could even be made compatible with current or experimental new diagnostics (Cirillo et al., 1995). Although recent studies with subunit vaccines have been promising, so far these vaccines conferred shorter survival than BCG when tested in M. tuberculosis aerogenically challenged guinea pigs, underlying the problems to be solved with these types of vaccines (Baldwin et al., 1998). However, subunit vaccines also may be important for disease control in immunodeficient individuals or in areas where the standard skin test has diagnostic significance. Furthermore, a subunit vaccine may be useful to boost individuals previously vaccinated with BCG or those at risk of disease reactivation (Baldwin et al., 1998).

The generation of a new live-attenuated vaccine poses many research challenges. Genetic systems to manipulate M. bovis BCG and M. tuberculosis offer the greatest promise for the development of new and effective vaccines against mycobacterial infections. Methods for allelic replacement and transposon mutagenesis in slow-growing mycobacteria have been reviewed (Pelicic et al., 1998). Using conditionally replicating genetic elements, two groups have reported major breakthroughs in the genetic manipulation of M. tuberculosis (Bardarov et al., 1997; Pelicic et al., 1997). Methods to generate unmarked deletion mutations in M. smegmatis, BCG, and M. tuberculosis have been described (Pavelka & Jacobs, 1999). This technology coupled with the knowledge of the M. tuberculosis genetic blueprint (Cole et al., 1998) should provide novel strategies for the rational development of live attenuated vaccines. The most promising approach for vaccine development would be to start with virulent M. tuberculosis microorganisms and generate attenuated mutants. These mutants should carry at least two attenuating deletion mutations and no antibiotic resistant markers, so as to avoid unwanted reversions or transfers of drug-resistance. It is contemplated that vaccine strains generated by the method of the present invention will include one or more additional mutations. Other important issues to consider are a) the degree of attenuation: mutants that are too attenuated may not induce protective immunity as it was the case for S. typhimurium phoP mutants (Fields et al., 1989); and b) whether the effect of the vaccine strain could be potentiated by co-administration of cytokines or by endowing the engineered strain with the capability to produce cytokines or phagosome membrane disrupters as lysteriolysin. In this case, temporal expression of these genes may be critical and may have to be regulated by promoters solely active inside phagocytic cells, as for example the promoter of the mig gene, first identified in M. avium (Plum & Clark-Curtiss, 1994) with a corresponding homologue (fadD19) found in the M. tuberculosis genome sequence (Cole et al., 1998).

Candidate genes for attenuating mutations may be those directly involved in the pathogenic process or those encoding housekeeping enzymes whose suppression may alter the ability of M. tuberculosis to survive and/or replicate within phagocytes. The best documented examples of mutations leading to attenuated phenotypes in vivo are the inactivations or deletions of the M. tuberculosis genes erp (Berthet et al., 1998), hma (Dubnau et al., 2000), katG (Li et al., 1998), leuD (Hondalus et al., 2000), mgtC (Buchmeier et al., 2000), and the recently described cyclopropane synthetase gene pcaA (umaA2) involved in cord formation (Glickman et al., 2000), and purC (Jackson et al., 1999). In addition, a M. tuberculosis deletion mutant unable to synthesize mycobactin was generated and shown to be impaired for growth in a human macrophage cell line (De Voss et al., 2000). Additional candidate genes and previous work has been summarized elsewhere (Cole et al., 1998). Other candidates are unidentified mycobacterial genes such as those involved in the inhibition of phagosome acidification (Sturgill-Koszycki et al., 1994; Via et al., 1998). It may be also possible to identify and inactivate genes responsible for subtle changes in the structure of lipoarabinomannan since these changes influence receptor-mediated uptake and ultimately intracellular fate and overall virulence (Kang & Schlesinger, 1998). Another approach that has been followed for the attenuation of M. tuberculosis is to engineer a recombinant strain overexpressing a global negative regulator of virulence genes. In this context, it was found that a recombinant M. tuberculosis carrying a dominant constitutively active iron repressor was attenuated in mice (Manabe et al. 1999). The above literature also describes standard methods for testing candidate vaccine strains in animal model systems such as mice or guinea pigs.

It was discovered that M. smegmatis alrA mutants display an increased susceptibility to bactericidal action of phagocytic cells such as macrophages (Chacon, O., 2002, incorporated herein by reference.) Based on this finding, pathogenic species of mycobacteria having an inactivated alrA gene could be constructed using methods known in the art. Such strains would be useful for the generation of attenuated live-attenuated vaccine candidates against *tuberculosis* and other human or animal diseases caused by mycobacteria such as leprosy and Crohn's disease and Johne's disease. Further, based on the discovery that alrA mutants are impaired in the ability to synthesize the basic building block of cell walls, peptidoglycan, vaccine strains which undergo spontaneous lysis in vivo can be constructed using methods known in the art. Lysis would allow for improved antigen delivery and containment of the vaccine strain.

To determine the effect of the inactivation of the alrA gene on the intracellular survival of *M. smegmatis* in phagocytic cells, monolayers of human macrophages were infected with wild type, mutant and recombinant control strains. Prior to infection, *M. smegmatis* strains were grown in medium supplemented with D-alanine which results in approximately the same rate of growth for all strains. Growth in monolayers was carried out in absence of D-alanine to approximate the conditions expected in the host. Monolayers were infected with *M. smegmatis* strains at a multiplicity of approximately 10 bacilli per cell, invasion was allowed to proceed for 2 h and extracellular bacteria were removed. At 24, 48 and 72 h post-infection, the number of intracellular surviving bacteria was determined as described in Materials and Methods. As expected, the wild type strain $mc^2155$ displayed moderate survival in monolayers of adherent human macrophages, with about 5-fold reduction in the number of intracellular bacteria after 72 h of incubation of the monolayers. In contrast, the alrA mutant strain TAM23 was less able to survive reaching a 5-fold reduction in intracellular bacilli at 24 h and 500-fold by 72 h. Thus, the inactivation of the alrA gene has a significant effect on the ability of *M. smegmatis* to survive within phagocytic cells.

To verify that the decreased survival of the mutant strain was due to the inactivation of the alrA gene, *M. smegmatis* TAM23 was complemented with a wild type copy which was delivered into the chromosome using an integrating vector. Strain TAM23(pTAMU3), carrying both the inactivated and wild type copies of the alrA gene, displayed wild type survival in human macrophages. This result confirmed that the inactivation of the alrA gene is responsible for the reduced survival of TAM23. In addition, the effects of introducing selection markers on the survival of *M. smegmatis* in phagocytic cells were tested using appropriate recombinant control strains. The kanamycin-resistant marker used to inactivate the alrA gene was introduced into the chromosome of the wild type strain via an integrating vector. The resulting recombinant strain $mc^2155$(pYUB178) displayed the same survival pattern as the wild type strain indicating that the introduction of this marker does not affect the intracellular survival of *M. smegmatis*. Since the vector used to complement the mutant strain carries a hygromycin-resistant marker, strain TAM23 was also transformed with this vector alone to generate the recombinant alrA mutant strain TAM23(pYUB412). In this case, the survival of this recombinant strain was slightly affected by the introduction of this marker. At 24 h post-infection, both TAM23 and TAM23(pYUB412) displayed a 5-fold reduction in intracellular survival; however at 48 and 72 h post-infection, TAM23(pYUB412) displayed an intermediate level of survival when compared to the wild type and TAM23 mutant strains. (FIG. 4). Thus, the hygromycin resistant marker has an influence on intracellular survival at longer times post-infection. Nonetheless, the effect is minor and significantly different from the complete recovery of the survival of TAM23 conferred, at every time-point post-infection, by the hygromycin-resistant integrating vector pTAMU3 carrying the wild type gene.

Method of Use: Identification of New Antimycobacterial Agents

In addition to new effective vaccines against mycobacteria, there is also an urgent need to develop new antimycobacterial agents. These new agents should be effective against these microorganisms without being toxic to the mammalian host. Drug therapy is the major approach to treat human mycobacterioses. Several primary and secondary anti-mycobacterial agents are currently used to treat human *tuberculosis*. The Food and Drug Administration has approved the following drugs as primary agents: ethambutol, isoniazid, pyrazynamide, rifampin, and streptomycin. Examples of approved second-line drugs are: amikacin, ciprofloxacine, cycloserine, ethionamide, and para-aminosalicylic acid. Recommended treatments use combination therapies with three agents for at least six months. However, these regimens are becoming ineffective due to the emergence of drug resistance strains, including the appearance of clinical isolates with multiple resistances to various primary and secondary drugs (Edlin et al., 1992; Kochi et al., 1993; Musser & Barry 1998). Thus, there is an urgent need to develop new and more effective anti-*tuberculosis* drugs.

Recent studies on mycobacterial drug resistance have focused on the study of specific biochemical targets of the primary and secondary drugs (Musser et al., 1999). For a summary of the principal targets identified to date, see Chacon, Ph.D. Thesis 2002, incorporated herein in its entirety. In all these cases, the common theme is that these targets are enzymatic proteins involved in key metabolic processes for the *Mycobacterium*. Identification and biochemical analysis of these proteins is then applied to the rational design of new and more effective anti-mycobacterial agents (Zhang & Telenti, 2000). Furthermore, genes encoding for some of these proteins may also serve as targets for the generation of attenuated strains that could be useful in developing effective vaccines against mycobacteria. This might be the case with genes playing an important role in metabolic pathways that are necessary for the biosynthesis of mycobacterial structural components. One of these genes, involved in the biosynthesis of peptidoglycan, is the alrA gene. The present invention is equally applicable to other mycobacterial genes involved in the synthesis of D-alanine.

The inhibition of AlrA by DCS in a concentration-dependent manner indicates that this enzyme serves as one of the drug targets (Caceres et al, 1997). However, the dispensability of the alrA gene for growth in vitro suggests that it is not the main target responsible for the bactericidal effect of DCS. Since overproduction of the enzyme leads to increased resistance to DCS, it appears that binding of DCS to AlrA protects another target within the cell. This hypothesis predicts that AlrA null mutants would be hypersusceptible to DCS. Thus, the corresponding MICs for wild-type and TAM23 alrA mutant strains were determined.

For MIC tests, *M. smegmatis* cells grown with and without n-alanine were inoculated onto complete Middlebrook MADC broth without D-alanine. The MIC of DCS for the wild-type strain was 75 $\mu$g/ml, independent of the presence of D-alanine in the original inoculum (Table 2). As expected, TAM23 was about 30-fold more sensitive (MIC, 2.56 $\mu$g/ml) when the inoculum was grown without D-alanine. Since TAM23 cells carry a mutation in a gene responsible for D-alanine biosynthesis, it is possible that growth in the presence of D-alanine partially restores wild-type MICs of DCS. To test this hypothesis, TAM23 was grown with D-alanine, harvested, washed extensively to prevent D-alanine carryover, and inoculated into the MIC test cultures. These conditions resulted in a fourfold increase in the MIC (MIC, 10.2), still about 7.5 times lower than the MIC for the wild-type strain. As a control, the MICs of the unrelated drugs amikacin, ethambutol, and rifabutin were also determined. The MICs for both wild-type and mutant strains were the same, independently of the presence or absence of D-alanine in the medium used to grow the inocula to determine the MICs. The effect of the addition of D-alanine directly into the MIC test cultures was also determined. D-Alanine would be expected to effectively compete with DCS and decrease the susceptibilities of both strains to DCS. As expected, under these conditions, the MIC of DCS for both wild-type and TAM23 strains increased dramatically to 1,200 μg/ml independently of prior growth conditions of the inocula. No significant differences were observed for the other unrelated drugs, demonstrating that the effect was specific for DCS. Complementation of strain TAM23 with the integrating vector pTAMU3, which carries the wild-type air gene, resulted in a strain for which the MICs were identical to those for the wild type.

TABLE 2

Minimal inhibitory concentrations of *M. smegmatis* wild type and TAM23 alr mutant strains to selected antimycobacterial agents determined with inocula grown with or without D-alanine.

| | Minimal Inhibitory Concentration[a] (MIC, μg/ml) | | | |
|---|---|---|---|---|
| | Wild Type mc$^2$ 155 | | TAM23 alr Mutant | |
| Drug | Without D-alanine[b] | With D-alanine[c] | Without D-alanine[b] | With D-alanine[c] |
| Amikacin | 1.56 | N.D. | 1.56 | 1.56 |
| D-Cycloserine | 75.0 | 75.0 | 2.56 | 10.2 |
| Ethambutol | 3.13 | N.D. | 3.13 | 3.13 |
| Rifabutin | 2.00 | N.D. | 2.00 | 1.00 |

[a]MICs were determined in complete Middlebrook 7H9 medium as described in Materials and Methods. For a given drug, MIC differences of the two strains are considered significant when values correspond to a separation of at least two doubling dilutions.
[b]Inoculum was grown in complete Middlebrook 7H9 medium without D-alanine supplementation, as described in Materials and Methods.
[c]Inoculum was grown in complete Middlebrook 7H9 medium supplemented with 50 mM D-alanine, as described in Materials and Methods.

This increased susceptibility indicated by the MIC growth inhibition data was also confirmed by the analysis of the bactericidal action of DCS in broth cultures grown in absence of D-alanine. Pilot experiments were performed with each strain to determine the optimal DCS concentration that resulted in a strong bactericidal effect. In the final experiment, cultures were grown to an early exponential phase ($OD_{600}$ of ~0.4), split in two, and DCS was added to one of these subcultures at 50 times the MIC. In absence of DCS, both the wild-type strain mc$^2$155 and the TAM23 mutant cells grew to a $OD_{600}$ of >2.0 and reached saturation at a cell density approximately above 5.0×10. These data also confirmed the independence of *M smegmatis* air mutants on D-alanine for growth and further demonstrate that air mutants can grow in absence of D-alanine at approximately the same growth rate as wild-type cells. In contrast, in the presence of DCS both cells underwent rapid death by lysis as revealed by both the drastic decrease observed in optical density and viable counts. Furthermore, the kinetic of killing was similar for both the wild-type and mutant strains. However, it must be emphasized that considering absolute drug concentrations, the effect on the mutant strain is observed at a 30-fold-lower concentration than for the wild-type strain. This pattern suggests that the bactericidal action of DCS is due to the inhibition of a more fundamental target different from AlrA.

An alternative explanation for the increased susceptibility of the null mutants to DCS is that the inactivation of the alrA gene changes the permeability of the cell wall to DCS. This alteration may not be detectable by morphological studies. To test this hypothesis, a methodology to perform DCS uptake assays was developed. The results obtained were similar for both wild-type and mutant strains. D-alanine uptake assays using a standardized procedure obtaining similar results for both strains was also carried out. Thus, a permeability change was ruled out as responsible for the observed phenotype of the null mutants.

The uptakes of D-alanine and DCS in both wild-type and mutant strains were not significantly different, indicating that changes in cell wall permeability are not a likely explanation for the DCS increased susceptible phenotype of the alrA mutant strain. Thus, the increased susceptibility of TAM23 cells to DCS is consistent with the existence of multiple targets for DCS. Our previous studies identified D-alanine racemase as one of these targets (Caceres et al, 1997). The lack of the racemase protein in the alrA mutant strain may lead to a hypersusceptible phenotype since more DCS would be required to inhibit both the racemase and an additional target(s) in the wild-type strain. In contrast, the bactericidal effect of DCS suggests the existence of another lethal target. In this context, D-alanine ligase is an attractive candidate since this enzyme activity is also inhibited by DCS (David, 1969; Chacon, Ph.D. thesis). More importantly, the construction of a conditionally lethal mutant bank led to the isolation of a thermosensitive mutant impaired in this gene function (Belanger et al., 2000). Furthermore, increased DCS susceptibility may reflect an alteration of the peptidoglycan structure of TAM23 cells, as a direct consequence of the inactivation of the alr gene. In this context, TAM23 cells were also more susceptible to DCS than were wild-type cells when grown in medium with D-alanine, but mutant cells grown without D-alanine displayed increased susceptible to both growth inhibition and the bactericidal action of DCS.

Based on the finding that inactivation of the alrA gene of *M. smegmatis* yielded a strain with increased susceptibility to D-alanine analogs, the generation of Alr null mutants as vaccine candidates would be possible using methods known in the art. The present invention accordingly seeks to provide novel live-attenuated mycobacteria as vaccines. Such vaccines would be especially effective for treatment of immunosuppressed patients, or others displaying signs of disease, with drugs such as D-alanine analogs.

Method of Use: Use of D-Alanine Racemase Mutants to Identify New Pathways of D-Alanine Biosynthesis It was discovered that *M. smegmatis* D-alanine racemase mutants can synthesize D-alanine by verifying the presence of D-alanine within the internal amino acid pool of TAM23. To determine the gene(s) responsible for the alternative pathway of D-alanine biosynthesis, the following procedure is followed: 1) a transposon mutant bank of TAM23 is constructed, 2) mutants are screened for the ability to grow in the presence or absence of D-alanine in the growth medium, 3) mutants unable to grow in the absence of D-alanine are identified by replica, 4) the region containing the transposon is cloned, and 5) the gene inactivated by the transposon is identified by DNA sequencing. Alternatively, a proteomic analysis of TAM23 can be performed before and after a shift from medium with D-alanine to media without D-alanine. Proteins induced under the latter conditions are candidates for enzymes involved in an alternative pathway of D-alanine biosynthesis. Protein spots are sequenced, and the coding gene(s) are identified and then inactivated to construct strains carrying multiple mutations. These strains are evaluated for their dependency on D-alanine for growth.

Based on the finding that TAM23 mutant of *M. smegmatis* was independent of D-alanine for growth, the inactivation of the alrA gene provides a means to study alternate metabolic pathways related to peptidoglycan synthesis in pathogenic mycobacteria. The discovery that mycobacteria possess a novel pathway of peptidoglycan synthesis, makes possible the exploitation, using methods known in the art, of such in the generation of other attenuated strains and new antimycobacterial drugs. The present invention accordingly seeks to provide novel AlrA null mutant mycobacterial strains for use in determining alternate metabolic pathways of D-alanine and/or peptidoglycan biosynthesis in the identification of drug targets for development of new bactericidal agents for the treatment of mycobacterial diseases.

Method of Use: Use of a DCS Hyper-Susceptible Mutant to Screen for Cell Wall Inhibitors An alrA mutant can be used to screen for inhibitors of peptidoglycan synthesis following methods known in the art (Kamogashira and Takegata, 1988, incorporated herein by reference).

EXAMPLES

The present invention is further described in the following examples, which are offered by way of illustration and are not intended to limit the invention in any manner. Standard techniques well known in the art or the techniques described below are utilized in the practice of the present invention.

Example 1

Generation of *M. smegmatis* alrA Mutants

Bacterial strains, plasmids, and culture conditions. Bacterial strains and plasmids used in this study are listed in Table 1. *E. coli* strains were grown at 37C in Luria-Bertani broth or agar. *M. smegmatis* strains were routinely grown at 37C in Middlebrook 7H9 base broth or agar (BBL Microbiology Systems, Cockeysville, Md.) supplemented with 0.5% bovine serum albumin fraction V (EM Science, Gibbstown, N.J.), 0.01 M dextrose (Sigma Chemical Co., St. Louis, Mo.), 0.015 M sodium chloride, and 0.2% glycerol (MADC). Broth medium was also supplemented with 0.05% Tween go (Sigma), and solid medium was made with 1.5% Bacto Agar (Difco Laboratories, Detroit, Mich.). When required, 0-alanine (Sigma) was used at 50 mM. Liquid cultures were incubated with shaking at 200 rpm in an Innova 4300 rotary incubator (New Brunswick Scientific Co. Inc., Edison, N.J.). As needed, the following antibiotics were used at the specified concentrations: ampicillin (Sigma), 50 µg/ml for *E. coli*; kanamycin A monosulfate (Sigma), 25 µg/ml for *E. coli* and 20 µg/ml for *M. smegmatis*; hygromycin B (Roche Molecular Biochemicals, Indianapolis, Ind.), 100 µg/ml for *E. coli* and *M. smegmatis*. For some experiments, *M. smegmatis* was grown in a broth minimal medium based on the formulation of Zygmunt, 1963, as modified by Caceres, 1999. Components and final concentrations were 5.0 mM ammonium chloride, $6.8\times10^{-7}$ mM calcium chloride, $8.4\times10^{-7}$ mM cobalt(II) chloride, 22 mM dibasic potassium phosphate, $2.5\times10^{-10}$ mM ferric chloride, 21 mM glycerol, 2.4 mM magnesium sulfate, $1.0\times10^{-5}$ mM manganese chloride, 16 mM monobasic potassium phosphate, $4.9\times10^{-6}$ mM pyridoxal hydrochloride, 0.4 mM Tween 80, and $8.6\times10^{-6}$ mM zinc sulfate. Individual chemicals were purchased from Sigma.

Bacterial transformation. *E. coli* was transformed as previously described (Ausubel et al., 1990). For the generation of *M. smegmatis* alrA mutants, 50 ml of an early exponential phase culture of *M. smegmatis* mc2155 was washed twice and concentrated 100-fold in cold 10% ultrapure glycerol (Invitrogen Life Technologies, Carlsbad, Calif.). Concentrated cells were electroporated with approximately 5.0 µg of the BamHI-KpnI fragment of pTAMU2 carrying the inactivated alrA gene. Electroporation was carried out at 2,500 V. 100 µF, and 246 Ω in an electrocell manipulator (model 600; BTX Inc., San Diego, Calif.). Electroporated cells were allowed to recover at 37C in MADC broth and plated on MADC agar supplemented with 50 mM D-alanine (Sigma) and kanamycin (20 µg/ml; Sigma). For the genetic complementation experiment, 50 ml of an early-exponential phase culture of *M. smegmatis* TAM23 alrA mutant was electroporated with 1.5 mg of pTAMU3 DNA at 2,500 V, 25 µF, and 1,000 Ω in a Gene Pulser electrocell manipulator (Bio-Rad Laboratories, Richmond, Calif.), as previously described (Foley et al., 1995). Transformants were selected on MADC agar supplemented with hygromycin (100 µg/ml; Roche).

Nucleic acid manipulations. Mycobacterial DNA was isolated by the standard method using cetyl trimethyl ammonium bromide (Ausubel, 1990). Plasmid DNA was isolated by an alkaline lysis method as previously described (Sambrook, 1989), using a large-scale isolation kit (Promega, Madison, Wis.) as recommended by the manufacturer. DNA fragments used for plasmid construction in *E. coli* and for recombination experiments in *M. smegmatis* were purified by gel electrophoresis and recovered by absorption to glass particles (GeneClean Bin 101, Vista, Calif.) as recommended by the manufacturer. Standard procedures were followed for restriction digestions, ligations, and agarose gel electrophoreses (Sambrook, 1989).

Amplification of the alrA gene was carried out with 50 ng of *M. smegmatis* genomic DNA template using primers NAN-1 and NAN-2 for 27 cycles in a thermal cycler (Perkin-Elmer Gene Amp PCR System 2400; Roche Molecular Systems, Branchhurg, N.J.) as previously described (Caceres, 1997). For Southern blotting analysis, approximately 3.0 µg of *M. smegmatis* genomic DNA was digested with SmaI, and DNA fragments were separated on a 0.8% agarose gel, subjected to an alkaline denaturing procedure, and transferred to Biotrans nylon membranes (ICN Biomedicals, Inc., Costa Mesa, Calif.). Membranes were hybridized with a probe corresponding to the 1.9-kb BamHI/PvuII fragment containing the wild-type *M. smegmatis* alr gene, which was radiolabeled with [α-32P]dCTP using the Rediprime DNA labeling II system (Amersham Pharmacia Biotech, Inc., Piscataway, N.J.) as recommended by the manufacturer. Prehybridization and hybridization were performed at 56C. Washes were done under high-stringency conditions at 65C as previously described (Sambrook, 1989).

Gram staining and acid-alcohol resistance testing. *M. smegmatis* cells were stained by the crystal violet method using a Gram stain kit (Sigma) as recommended by the manufacturer. Acid-alcohol resistance was determined by the Zielsi-Neelsen acid-fast procedure using the TB Stain Kit ZN (Difco), as recommended by the manufacturer.

Electron microscopy. Strains were grown to an optical density at 600 nm (OD655) of approximately 1.0 in MADC- Tween, with or without D-alanine. Cells were harvested, washed twice with phosphate-buffered saline (PBS)-0.05% Tween, and fixed for 1 h in 2.5% buffered glutaraldehyde, washed twice, and postfixed with 2.0% osmium tetroxide. After repeated washings in PBS, samples were dehydrated in a graded series of ethanol solutions, washed twice in propylene oxide, and embedded with Araldite resin. Thin sections were examined with a Philips 201 transmission electron microscope (Philips Electron Optics, Eindhovetn The Netherlands) at an accelerating voltage of 60 kV.

D-Alanine racemase assays. Approximately 200-ml cultures of M. smegmatis mc2155 or TAM23 were grown in MADC-Tween with or without D-alanine until they reached an $OD_{600}$ of ca. 1.0. Cultures were washed twice and concentrated 50-fold in 50 mM Tris-HCl (pH 8.0). Cells were sonicated on a salt-ice-water bath with a Vibra-Cell model VC600 sonicator (Sonic and Materials, Inc., Danbury, Conn.). Sonication was carried out for 2 min at 80% power output and 50% duty cycle, and in the presence of 30% (vol/vol) type A-5 alumina (Sigma). The resulting active cell extracts were centrifuged at 4C in a JA-17 rotor (Beckman Instruments, Inc., Fullerton, Calif.) for 30 mm at 15,000 rpm, dialyzed against 50 mM Tris-HCl(pH 8.0), and sterilized by filtration through a 0.22-$\mu$-poresize filter (Advantec MFS Inc., Pleasanton, Calif.). Protein concentration was determined by the DC assay (Bio-Rad) as recommended by the manufacturer. Alr activity in the active cell extracts was assayed in the direction of the conversion of L-alanine into D-alanine by a modification of the coupled-spectrophotometric method previously described (Caceres, 1999). To start the reactions, active crude cell extracts were added to 1.0 ml of prewarmed mixtures containing 50 mM Tris-HCl (pH 8.0), 0.1 mM pyridoxal phosphate (Sigma), and 15 mM L-alanine (Sigma). After 15 min of incubation at 37C, when the conversion of substrate into product remains linear, reactions were stopped by boiling for 10 min. Subsequently, 1 U of d-amino acid oxidase (Calzyme, San Lois Obispo, Calif.), 0.2 mM NADH (Roche Laboratories), and 10 U of rabbit muscle lactic dehydrogenase (Sigma) were added. The coupled reaction was measured by the change in absorbance at 340 nm after 5 h of incubation at 37C. All samples were measured in triplicate. Specific activities (in micromoles of consumed substrate minute-1 milligram-1) were calculated as previously described (Caceres et al, 1997).

LDH assays. L-Lactate dehydrogenase (LDH) activity endogenous to crude cell extracts of M. smegmatis was measured in the direction of the conversion of pyruvate into lactate coupled to the oxidation of NADH as previously described in the Worthington enzyme manual (Worthington Biochemical Corp., Lakewood, N.J.). Crude cell extracts were added to 1.0 ml of prewarmed mixtures containing 50 mM Tris-HCl (pH 8.0), 1.0 mM sodium pyruvate (Sigma), and 0.2 mM NADH (Roche). The change in absorbance at 340 nm was measured after 1 h of incubation at 37C. All samples were measured in triplicate. Specific activities (in micromoles of consumed substrate minute-1 milligram-1) were calculated as described in the enzyme manual mentioned above by subtracting the background change in absorbance (obtained from boiled inactivated extracts processed in identical manner) from the change in absorbance obtained with the active cell extracts.

Example 2

Generation of M. tuberculosis alrA Mutants

Example 3

Drug Susceptibility Assays

MICs were determined by a microplate twofold dilution method, as described by Takiff et al., 1996, with modifications. M. smegmatis* $mc^2155$ and TAM23 cells were grown in 25 ml of MADC-Tween with and without 50 mM D-alanine to an $OD_{600}$ of approximately 1.0. Bacteria were washed with PBS-Tween, and 105 CFU was inoculated onto each well containing serial twofold dilutions of various antimicrobial agents. Plates were incubated at 37C, and visual inspection to determine MICs was carried out at 48 h. The MIC is defined as the lowest concentration that prevents observable bacterial growth and is determined by the consistent result of three independent cultures, each assayed in triplicate.

*M. smegmatis* strains $mc^2155$ and TAM23 were grown in MADC-Tween broth at 37C to an $OD_{600}$ of ca. 0.5. These starter cultures were used to inoculate 200 ml of MADC broth, and cells were then grown to an $OD_{600}$ of ca. 0.4. Two 50-ml aliquots of these exponentially growing cultures were transferred to separate flasks. DCS was added to one of the corresponding cultures, with the other serving as a growth control. Concentrations of DCS were 50 times the MIC for each strain (3.75 mg/ml for $mc^2155$ and 128 $\mu$g/ml for TAM23). All cultures were incubated at 37C in a shaking incubator for 72 h. The $OD_{600}$ was measured for each culture at 3, 6, 9, 12, 24, 48, and 72 h. Concurrently, aliquots were taken, serially diluted, and plated onto MADC agar in triplicate to determine numbers of viable bacterial counts.

Example 4

D-Alanine Uptake Assays

For D-alanine uptake assays, the method described by David, 1971, was used. Cells exponentially growing in MADC-Tween ($OD_{600}$, ca. 1.0) were collected by centrifugation at 40C, washed once in ice-cold 50 mM Tris-HCl buffer (pH 8.0) containing 0.05% Tween 80, and concentrated 20 times in the same buffer. Samples were prewarmed for 10 min at 37C, and D-alanine was added to a final specific activity of 3.0 $\mu$Ci of [14C]-1-D-alanine (ICN) per $\mu$mol asid 0.2 mM concentration. Samples were placed in a 37C water bath. Aliquots were taken at various times and immediately placed on ice. The sample for each time point was divided in three subsample triplicates of 0.5 ml and filtered through 0.8-$\mu$m-pore-size membrane filters (Millipore Corp., Bedford, Mass.) in a manifold. Each filter was washed three times with 10 ml of cold buffer, dried under a heat lamp, and weighed. The cell-associated radioactivity was determined in a liquid scintillation counter (Wallac 1410; Pharmacia, Piscataway, N.J.) using EcoLite scintillation cocktail (ICN). Uptake data were expressed as micromoles of D-alanine per milligram (dry cell weight).

Since radiolabeled DCS is not commercially available, an uptake assay was developed based on the colorimetric determination of this compound (Jones, 1956). Cells exponentially growing in MADC-Tween ($OD_{600}$ of ~1.0) were harvested at 4C by centrifugation, washed twice with water, and concentrated 40 times. Samples were prewarmed at 37C for 10 min, and DCS was added to a final concentration of 250 $\mu$g/ml (~2.5 mM). Cells were placed in a 37C water bath. Aliquots were taken at various times and immediately placed on ice. After 20 min of incubation, clumping of TAM23 cells was evident and uptake determinations became unreliable. Each time a point sample was washed twice with water, resuspended, and sonicated. Protein concentration was determined using the Bio-Rad DC assay, followed by protein removal through serial passages of both YM-10 and YM-3 Centricon concentrators (Millipore Corp.). The concentration of DCS was determined by measuring the OD620 after adding a specific color-developing reagent as previously described (Jones, 1956). A standard curve was generated by diluting a DCS standard in a cell extract that was prepared from cells not exposed to DCS. Uptake data were expressed as micromoles of DCS per milligram of protein. Since D-alanine and DCS uptake assays do not measure the same parameters, reported values for each assay cannot be directly compared.

Example 5

Increased Susceptibility to Phagocytic Cells

Intracellular killing assays were carried out as described previously with the following modifications (Bermudez and Young, 1988). Approximately $5 \times 10^5$ monocytes were seeded on each well of a 24-well tissue culture plate (Sigma). Plates were incubated for 2 h at 37 C in 5% $CO_2$. Supernatant fluids with nonadherent cells were removed and the wells were washed twice with 1.0 ml of prewarmed HBSS. The adherent monocytes were maintained in culture for 7 days with 1.5 ml of RPMI 1640 (Gibco) supplemented with 2 mM L-glutamine (Sigma) and 10% heat-inactivated fetal bovine serum (Sigma). Culture media was replaced every 48 hours. Each well was inoculated with approximately $5.0 \times 10^6$ CFU of bacteria. After 2 h, macrophage monolayers were washed three times with HBSS to remove extracellular microorganisms. Some wells were lysed immediately with 0.5 ml of sterile water for 10 min and 0.025% SDS (Sigma) in HBSS for additional 10 min. SDS was subsequently inactivated with 0.1% bovine albumin (Sigma). The lysate was serially diluted and plated onto Middlebrook 7H9 based agar (BBL) supplemented with 0.5% fraction V albumin (EM Science), 0.01 M dextrose (Sigma), 0.015 M sodium chloride (Sigma), 0.15% glycerol (Sigma) and 1.5% Bacto agar (Difco). The same procedure was done on two other sets of wells at 24, 48 and 72 hours. Three wells were carried out per experimental group, in each of three independent experiments. It is to be noted that a preliminary experiment using 20 μg/ml of amikacin during the invasion step to kill extracellular bacteria yielded similar results, demonstrating the effectiveness of the washing procedure.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

BIBLIOGRAPHY

Ausubel, F. M., R. Brent, R. E. Kingston, D. D. Moore, J. G. Seidman, J. A. Smith, and K. Struhl (ed.). 1990. Current protocols in molecular biology. Greene Publishing Associates and Wiley-Interscience, New York, N.Y.

Baldwin, S. L., D'Souza C., Roberts, A. D., Kelly, B. P., Frank, A. A., Lui, M. A., Ulmer, J. B., Huygen, K., McMurray, D. M. & Orme, I. M. (1998). Evaluation of new vaccines in the mouse and guinea pig model of *tuberculosis*. Infect Immun 66, 2951–2059.

Bardarov S., Kriakov J., Carriere C., Yu S., Vaamonde C., McAdam R A., Bloom B R., Hatfull G F., Jacobs W R. Jr. 1997. Conditionally replicating mycobacteriophages: a system for transposon delivery to *Mycobacterium tuberculosis*. Proc. Natl. Acad. Sci. USA 94:10961–10966.

Barletta, R. G., Snapper, S. B., Cirillo, J. D., Connell, N. D., Kim, D. D., Jacobs, W. R., Jr. & Bloom, B. R. (1990). Recombinant BCG as a candidate oral vaccine. Res. Microbiol. 141, 931–939.

Belanger, A. E., and J. M. Inamine. 2000. Genetics of cell wall biosynthesis, p. 191–202. In G. F. Hatfull and W. R. Jacobs, Jr. (ed.), Molecular genetics of mycobacteria. ASM Press, Washington, D.C.

Belanger, A. E., J. C. Porter, and G. F. Hatfull. 2000. Genetic analysis of peptidoglycan biosynthesis in mycobacteria: characterization of a ddlA mutant of *Mycobacterium smegmatis*. J. Bacteriol. 182:6854–6856.

Bermudez, L. E. & Yound, L. S. (1988). Tumor necrosis factor, alone or combination with IL-2, but not IFN-gamma, is associated with macrophage killing of *Mycobacterium avium* complex. J Immunol 140, 3006–3013.

Berthet, F. X., Lagranderie, M., Gounon, P., C., L. W., Ensergueix, D., Chavarot, P., Thouron, F., Maranghi, E., Pelicic, V., Portnoi, D., Marchal, G. & Giequel, B. (1998). Attenuation of virulence by disruption of the *Mycobacterium tuberculosis* erp gene. Science 282, 759–762.

Blattner, F. R., V. Burland, G. Plunkett III, H. J. Sofia, and D. L. Daniels. 1993. Analysis of the *Escherichia coli* genome. IV. DNA sequence of the region from 89.2 to 92.8 minutes. Nucleic Acids Res. 21:5408–5417.

Bloom, B. R. & Murray, C. J. L. (1992), *Tuberculosis*: Commentary on a reemergent killer. Science 257, 1055–1064.

Braustein M., Bardarov S, Jacobs W R Jr. 2002. Genetic methods for deciphering virulence determinants of *Mycobacterium tuberculosis*. Meth Enzymol. 358:67–99.

Buchmeier, N., Blanc-Potard, A., Ehrt, S., Piddington, D., Riley, L. & Groisman, E. A. (2000). A parallel intraphagosomal survival strategy shared by *mycobacterium tuberculosis* and *Salmonella enterica*. Mol. Microbiol. 35, 1375–1382.

Cáceres, N. E., N. B. Harris, J. F. Wellehan, Z. Feng, V. Kapur, and R. G. Barletta. 1997. Overexpression of the D-alanine racemase gene confers resistance to D-cycloserine in *Mycobacterium smegmatis*. J. Bacteriol. 179:5046–5055.

Cáceres, N. E. 1999. Ph.D. thesis. University of Nebraska, Lincoln.

Carleton, P. (1993). Respiratory *tuberculosis*. In Pathology of Domestic Animals, pp. 493–502. Edited by K. V. F. Jubb, P. C. Kennedy & N. Palmer. Orlando, Fla.: Academic Press Inc.

Chacon, O. Isolation and characterization of *Mycobacterium smegmatis* D-analine racemase mutants. Ph.D. Thesis. Texas A&M University. December 2002.

Chaisson, R. E., C. A. Benson, M. P. Dube, L. B. Heifets, J. A. Korvick, S. Elkin, T. Smith, J. C. Craft, and F. R. Sattler. 1994. Clarithromycin therapy for bacteremic *Mycobacterium avium* complex disease. A randomized, double-blind, dose-ranging study in patients with AIDS. AIDS Clinical Trials Group Protocol 157 Study Team. Ann. Intern. Med. 121:905–911.

Chatterjee, D. 1997. The mycobacterial cell wall: structure, biosynthesis and sites of drug action. Curr. Opin. Chem. Biol. 1:579–588.

Cirillo J. D., T. R. Weisbrod, L. Pascopella, B. R. Bloom, and W. R. Jacobs, Jr. 1994. Isolation and characterization of the aspartokinase and aspartate semialdehyde dehydrogenase operon from mycobacteria. Mol. Microbiol. 11:629–639.

Cocito, C., Gilot, P., Coene, M., de Kesel, M., Poupart, P. & Vannuffel, P. (1994). Paratuberculosis. Clin. Microbiol. Rev 7, 328–345.

Cole, S. T., R. Brosch, J. Parkhill, T. Garnier, C. Churcher, D. Harris, S. V. Gordon, K. Eiglmeier, S. Gas, C. E. Barry III, F. Tekaia, K. Badcock, D. Basham, D. Brown, T. Chillingworth, R. Connor, D. Davies, K. Devlin, T. Feltwell, S. Gentles, N. Hamlin, S. Holroyd, T. Hornsby, K. Jagels, A. Krogh, J. McLean, S. Moule, L. Murphy, K. Oliver, J. Osborne, M. A. Quail, R. A. Rajandream, J. Rogers, S. Rutter, K. Seeger, J. Skelton, R. Squares, S. Squares, J. E. Sulston, K. Taylor, S. Whitehead, and B. G. Darrell. 1998. Deciphering the biology of Mycobacterium tuberculosis from the complete genome sequence. Nature 393:537–544.

Cummings, M. M., R. A. Patnode, and P. C. Hudgins. 1955. Effects of cycloserine on Mycobacterium tuberculosis in vitro. Anibiot. Chemother. 5:198–203.

Daffe, M., and P. Draper. 1998. The envelope layers of mycobacteria with reference to their pathogenicity. Adv. Microb. Physiol. 39:131–203.

David, H. L. 1971. Resistance to D-cycloserine in the tubercle bacilli: mutation rate and transport of alanine in parental cells and drug-resistant mutants. Appl. Microbiol. 21:888–892.

David, H. L., T. Takayama, and D. S. Goldman. 1969. Susceptibility of mycobacterial D-alanyl-D-alanine synthetase to D-cycloserine. Am. Rev. Respir. Dis. 100:579–581.

DeVoss, J. J., Rutter, K., Schroeder, B. G., Su, H., Zhu, Y. & Barry, C. E. 3$^{rd}$ (2000). The salicylate-derived mycobactin siderophores of Mycobacterium tuberculosis are essential for growth in macrophages. Proc Natl Acad Sci USA 97, 1252–1257.

Dubnau, E., chan, J., Raynaud, C., Mohan, V. P., Laneelle, M. A., Yu, K., Quemard, A. Smith, I. & Dafe, M. (2000). Oxygenated mycolic acids are necessary for virulence of in mice. Mol. Microbiol. 36, 630–637.

Dye, C., S. Scheele, P. Dolin, V. Pathania, and M. C. Raviglione. 1999. Consensus statement. Global burden of tuberculosis: estimated incidence, prevalence, and mortality by country. WHO Global Surveillance and Monitoring Project. JAMA 282:677–686.

Edlin, B. R., tokars, J. I., Grieco, M. H., Crawford, J. T., Williams, J., Sordillo, E. M., Ong, J. R., Kilburn, J. O., Dooley, S. W., Castro, K. G., Jarvis, W. R. & Holmberg, S. D. (1992). An outbreak of multidrug-resistant tuberculosis among hospitalized patients with the acquired immunodeficiency syndrome. N Engl J Med 326, 1514–1521.

Espinal, M. A., S. J. Kim, P. G. Suarez, K. M. Kam, A. G. Khomenko, G. B. Migliori, J. Baez, A. Kochi, C. Dye, and M. C. Raviglione. 2000. Standard short-course chemotherapy for drug-resistant tuberculosis: treatment outcomes in 6 countries. JAMA 283:2537–2545.

Feng, Z. and Barletta, R. G. 2003. Roles of Mycobacterium smegmatis D-Alanine: D-Alanine Ligase and D-Alanine Racemase in the Mechanisms of Action of and Resistance to the Peptidoglycan Inhibitor D-Cycloserine. Antimicrob. Agents Chemother. 47(1).

Fields, P. I., Groisman, E. A. & Heffron, F. (1989). A Salmonella locus that controls resistance to microbicidal proteins from phagocytic cells. Science 243, 1059–1061.

Foley-Thomas, E. M., D. L. Whipple, L. E. Bermudez, and R. G. Barletta. 1995. Phage infection, transfection, and transformation of Mycobacterium avium complex and M. paratuberculosis. Microbiology 141:1173–1181.

Galakatos, N. G., E. Daub, D. Botstein, and W. T. Walsh. 1986. Biosynthetic alr alanine racemase from Salmonella typhimurium: DNA and protein sequence determination. Biochemistry 25:3255–3260.

Glickman, M. S., Cox, J. S., & Jacobs, W. R., Jr. (2000). A novel mycolic acid cyclopropane synthetase is required for cording, persistence, and virulence of Mycobacterium tuberculosis. Mol. Cell 5:717–727.

Harris N. B., Barletta R. G. Mycobacterium avium subsp. Paratuberculosis in Veterinary Medicine. Clin. Microbiol. Rev. 2001 14:489–512.

Hols, P., C. Defrenne, T. Ferain, S. Derzelle, B. Delplace, and J. Delcour. 1997. The alanine racemase gene is essential for growth of Lactobacillus plantarum. J. Bacteriol. 179:3804–3807.

Hondalus, M. K., Bardarov, S., Russell, R., Chan, J., Jacobs, W. R., Jr. & Bloom, B. R. (2000). Attenuation of and protection induced by a leucine auxotroph of Mycobacterium tuberculosis. Infect Immun 68, 2888–2898.

Inderlied, C. B., C. A. Kemper, and L. E. Bermudez. 1993. The Mycobacterium avium complex. Clin. Microbiol. Rev. 3:266–310.

Jackson, M., Phalen, S. W., Lagranderie, M., Ensergueix, D., Chavarot, P., Marchal, G., McMurray, D. N., Gicquel, B. & Guilhot, C. (1999). Persistence and protective efficacy of a Mycobacterium tuberculosis auxotroph vaccine. Infect Immun 67, 2867–2873.

Jacobs, W. R., Jr. 2000. Mycobacterium tuberculosis: a once genetically intractable organism, p. 1–36. In G. F. Hatfull and W. R. Jacobs, Jr. (ed.), Molecular genetics of mycobacteria. ASM Press, Washington, D.C.

Jones, L. R. 1956. Colorimetric determination of cycloserine, a new antibiotic. Anal. Chem. 28:39–41.

Julius, M., C. A. Free, and G. T. Barry. 1970. Alanine racemase (Pseudo-monas). Methods Enzymol. 17:171–176.

Kamogashira T. Takegata S. A screening method for cell wall inhibitors using a D-cycloserine hypersensitive mutant. J. Antibiot (Tokyo). 1988. 41:803–806.

Kang, B. K. & Schlesinger, L. S. (1998). Characterization of mannose receptor-dependent phagocytosis mediated by Mycobacterium tuberculosis lipoarabinomannan. Infect Immun 66, 2769–2777.

Kochi, A., Vareldzis, B. & Styblo, K. (1993). Multidrug-resistant tuberculosis and its control. Res. Microbiol. 144, 104–110.

Lambert, M. P., and F. C. Neuhaus. 1972. Mechanism of D-cycloserine action: alanine racemase from Escherichia coli W. J. Bacteriol. 110:978–987.

Lee, M. H., and G. F. Hatfull. 1993. Mycobacteriophage L5 integrase-mediated site-specific integration in vitro. J. Bacteriol. 175:6836–6841.

Li, Z., Kelley, C., Collins, R., Rouse, D. & Morris, S. (1998). Expression of katG in Mycobacterium tuberculosis is associated with its growth and persistence in mice and guinea pigs. J. Infect Dis 177, 1030–1035.

Lobocka, M., J. Hennig, J. Wild, and T. Klopotowski. 1994. Organization and expression of the Escherichia coli K-12 dad operon encoding the smaller subunit of D-amino acid dehydrogenase and the catabolic alanine racemase. J. Bacteriol. 176:1500–1510.

McNeil, M. R., and P. J. Brennan. 1991. Structure, function, and biogenesis of the cell envelope of mycobacteria in relation to bacterial physiology, pathogenesis and drug resistance; some thoughts and possibilities arising from recent structural information. Res. Microbiol. 142:451–463.

Manabe, U. C., Saviola, B. J., Sun, L., Murphy, J. R., & Bishai, W. R. (1999). Attenuation of virulence in Mycobacterium tuberculosis expressing a constitutively active iron repressor. Proc Natl Acad Sci USA 96, 12844–12848.

Musser, J. M. & Barry, C. E. 3rd, 1998. Inhibition of a *Mycobacterium tuberculosis* beta-ketoacyl ACP synthase by isoniazid. Science 280, 1607–1610.

Neuhaus, F. C. 1962. The enzymatic synthesis of D-alanyl-D-alanine. I. Purification and properties of D-alanyl-D-alanine synthetase. J. Biol. Chem. 237:778–786.

Neuhaus, F. C. 1967. D-cycloserine and O-carbamyl-D-serine, p. 40–83. In D. Gottlieb and P. L. Shaw (ed.), Antibiotics: mechanisms of action, vol. 1. Springer-Verlag, Heidelberg, Germany.

Neuhaus, F. C., and J. L. Lynch. 1964. The enzymatic synthesis of D-alanyl-D-alanine. III. On the inhibition of D-alanyl-D-alanine synthetase by the antibiotic D-cycloserine. Biochemistry 3:471–480.

Noordeen, S. K. (1991). A look at world leprosy. Lep Rev 62, 72–86.

O'Reilly, L. M. & Daborn, C. J. (1995). The epidemiology of *mycobacterium* bovis infections in animals and man: a review. Tuber Lung Dis. 76, Suppl. 1, 1–46.

Oka, A., H. Sugisaki, and M. Takanami. 1981. Nucleotide sequence of the kanamycin resistance transposon Tn903. J. Mol. Biol. 147:217–226.

Pascopella, L., F. M. Collins, J. M. Martin, M. H. Lee, G. F. Hatfull, C. K. Stover, B. R. Bloom, and W. R. Jacobs, Jr. 1994. Use of in vivo complementation in *Mycobacterium tuberculosis* to identify a genomic fragment associated with virulence. Infect. Immun. 62:1313–1319.

Pavelka, M. S., and W. R. Jacobs, Jr. 1996. Biosynthesis of diaminopimelate, the precursor of lysine and a component of peptidoglycan, is an essential function of *Mycobacterium smegmatis*. J. Bacteriol. 178:6496–6507.

Pavelka, M. S., and W. R. Jacobs, Jr. 1999. Comparison of the construction of unmarked deletion mutations in *Mycobacterium smegmatis, Mycobacterium bovis* bacillus Calmette-Guérin, and *Mycobacterium tuberculosis* H37Rv by allelic exchange. J. Bacteriol. 181:4780–4789.

Pelicic V., Jackson M., Reyrat J M., Jacobs W R Jr., Gicquel B., Guilhot C. 1997. Efficient allelic exchange and transposon mutagenesis in *Mycobacterium tuberculosis*. Proc. Natl. Acad. Sci. USA. 94:10955–10960.

Peteroy, M., A. Severin, F. Zhao, D. Rosner, U. Lopatin, H. Scherman, A. Belanger, B. Harvey, G. F. Hatfull, P. J. Brennan, and N. D. Connell. 2000. Characterization of a *Mycobacterium smegmatis* mutant that is simultaneously resistant to D-cycloserine and vancomycin. Antimicrob. Agents Chemother. 44:1701–1704.

Petit, J. F., A. Adam, J. Wietzerbin-Falszpan, E. Lederer, and J. M. Ghuysen. 1969. Chemical structure of the cell wall of *Mycobacterium smegmatis*. I. Isolation and partial characterization of the peptidoglycan. Biochem. Bio-phys. Res. Commun. 35:478–485.

Plum, G. & Clark-Curtiss, J. E. (1994). Induction of *Mycobacterium avium* gene expression following phagocytosis by human macrophages. Infect Immun 62, 476–483.

Pritchard, D. G. (1988). A century of bovine *tuberculosis* 1888–1988: conquest and controversy. Comp Pathol 99, 357–399.

Sambrook, J., E. F. Fritsch, and T. Maniatis. 1989. Molecular cloning: a laboratory manual, 2nd ed. Cold Spring Harbor Laboratory, Cold Spring Harbor, N.Y.

Snapper, S. B., R. E. Melton, S. Mustafa, T. Kieser, and W. R. Jacobs, Jr. 1990. Isolation and characterization of efficient plasmid transformation mutants of *Mycobacterium smegmatis*. Mol. Microbiol. 4:1911–1919.

Strominger, J. L. 1962. Biosynthesis of bacterial cell walls, p. 413–470. In I. C. Gunzalus and R. Y. Stanier (ed.), The bacteria, vol. III. Academic Press, Inc., New York, N.Y.

Sturgill-Koszycki, S., Schlesinger, P. H., Chakraborty, P., Haddix, P. L., Collins, H. L., Fok, A. K., Allen, R. D., Gluck, S. L., Heuser, J., & Russell, D. G. (1994). Lack of acidification in *Mycobacterium* phagosomes produced by exclusion of the vesicular proton-ATPase. Science 263, 678–681.

Strych, U., R. L. Penland, M. Jimenez, K. L. Krause, and M. J. Benedik. 2001. Characterization of the alanine racemases from two mycobacteria. FEMS Microbiol. Lett. 196:93–98.

Takiff, H. E., M. Cimino, M. C. Musso, T. Weisbrod, R. Martinez, M. B. Delgado, L. Salazar, B. R. Bloom, and W. R. Jacobs, Jr. 1996. Efflux pump of the proton antiporter family confers low-level fluoroquinolone resistance in *Mycobacterium smegmatis*. Proc. Natl. Acad. Sci. USA 93:362–366.

Telenti, A., W. J. Philipp, S. Sreevatsan, C. Bernasconi, K. E. Stockbauer, B. Wieles, J. M. Musser, and W. R. Jacobs, Jr. 1997. The emb operon, a gene cluster of *Mycobacterium tuberculosis* involved in resistance to ethambutol. Nat. Med. 3:567–570.

Thompson, R. J., H. G. Bouwer, D. A. Portnoy, and F. R. Frankel. 1998. Pathogenicity and immunogenicity of a *Listeria monocitogenes* strain that requires D-alanine for growth. Infect. Immun. 66:3552–3561.

Trias, J., and R. Benz. 1994. Permeability of the cell wall of *Mycobacterium smegmatis*. Mol. Microbiol. 14:283–290.

Van Heijenoort, J. 1996. Murein synthesis, p. 1025–1034. In F. C. Neidhardt, R. Curtiss III, J. L. Ingraham, E. C. C. Lin, K. B. Low, B. Magasanik, W. S. Reznikoff, M. Riley, M. Schaechter, and H. E. Umbarger (ed.), *Escherichia coli* and *Salmonella*: cellular and molecular biology, 2nd ed., vol. 1. ASM Press, Washington, D.C.

Via, L. E., Fratti, R. A., McFalone, M., Pagan-Ramos, E., Deretic, D., & Deretic, V. (1998). Effects of cytokines on mycobacterial phagosome maturation. J Cell Sci 111, 897–905.

Walsh, C. T. 1989. Enzymes in the D-alanine branch of bacterial cell wall peptidoglycan assembly. J. Biol. Chem. 264:2393–2396.

Wasserman, S. A., E. Daub, P. Grishif, D. Botstein, and C. T. Walsh. 1984. Catabolic alanine racemase from *Salmonella typhimurium*: DNA sequence, enzyme purification, and characterization. Biochemistry 23:5182–5187.

Wasserman, S. A., C. T. Walsh, and D. Botstein. 1983. Two alanine racemase genes in *Salmonella typhimurium* that differ in structure and function. J. Bacteriol. 153:1439–1450.

Wijsman, H. J. W. 1972. The characterization of an alanine racemase mutant of *Escherichia coli*. Genet. Res. 20:269–277.

Yew, W. W., C. F. Wong, P. C. Wong, J. Lee, and C. H. Chau. 1993. Adverse neurological reactions in patients with multidrug-resistant pulmonary *tuberculosis* after coadministration of cycloserine and ofloxacin. Clin. Infect. Dis. 17:288–289.

Zhang Y. & Telenti A. (2000). Genetics of drug resistance in *Mycobacterium tuberculosis*. In Molecular Genetics of Mycobacteria pp. 235–254. Edited by G. F. Hatfll & W. R. Jacobs, Jr., Washington, D.C.: ASM Press.

Zygmunt, W. A. 1963. Antagonism of D-cycloserine inhibition of mycobacterial growth by D-alanine. J. Bacteriol. 85:1217–1220.

What is claimed and desired to be secured by Letters Patent is as follows:

1. A recombinant *mycobacterium* comprising an inactivated alrA gene, wherein said *mycobacterium* is independent of D-alanine for growth.

2. The recombinant *mycobacterium* of claim 1, wherein said *mycobacterium* is selected from the group consisting of *Mycobacterium smegmatis*, and subspecies thereof.

3. The recombinant mycobacteria of claim 1, wherein said recombinant mycobacteria further comprises one or more additional mutation encoding peptide or non-peptide antigens from a pathogenic mycobacteria.

4. The recombinant mycobacteria of claim 1, wherein said recombinant mycobacteria displays increased susceptibility to an antimycobacterial agent.

5. The recombinant mycobacteria of claim 4, wherein said antimycobacterial agent is selected from the group consisting of D-cycloserine and other D-alanine analogs.

6. The recombinant mycobacteria of claim 1, wherein said recombinant mycobacteria further comprises one or more additional mutations, whereby said recombinant mycobacteria is rendered dependent on D-alanine for growth.

7. The recombinant mycobacteria of claim 1, wherein said recombinant mycobacteria displays increased susceptibility to bactericidal action of phagocytic cells.

8. The recombinant mycobacteria of claim 1, wherein said recombinant mycobacteria further comprises a single D-alanine ligase gene under the control of an inducible promoter, said promoter controlling the expression of D-alanyl-D-alanine.

9. The recombinant *mycobacterium* of claim 2, wherein said *mycobacterium* is a strain designated TAM20.

10. The recombinant *mycobacterium* of claim 2, wherein said *mycobacterium* is a strain designated TAM23.

* * * * *

UNITED STATES PATENT AND TRADEMARK OFFICE
CERTIFICATE OF CORRECTION

| | |
|---|---|
| PATENT NO. | : 6,929,799 B2 |
| APPLICATION NO. | : 10/323351 |
| DATED | : August 16, 2005 |
| INVENTOR(S) | : Raúl G. Barletta and Ofelia Barletta-Chacon |

It is certified that error appears in the above-identified patent and that said Letters Patent is hereby corrected as shown below:

Column 1
Line 14, delete " Cooperative State Research Service Project Grant No. NEB. 14-108."

Column 1
Line 14, replace with --/CSREES 98-35204-6761, NIH R03 AI051176-01.--

Signed and Sealed this

Eleventh Day of December, 2007

JON W. DUDAS
*Director of the United States Patent and Trademark Office*